(12) United States Patent
Bogdan et al.

(10) Patent No.: US 6,451,867 B1
(45) Date of Patent: Sep. 17, 2002

(54) MIXTURES CONTAINING 1,1,1,3,3-PENTAFLUOROPROPANE AND 1,1,1,3,3-PENTAFLUOROBUTANE

(75) Inventors: Mary Charlotte Bogdan, West Seneca; David John Williams, East Amherst; Leslie Bruce Bement; Ronald Riegal, both of Buffalo, all of NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/813,494

(22) Filed: Mar. 21, 2001

(51) Int. Cl.⁷ .............................. C08J 9/00; C07C 19/08
(52) U.S. Cl. .................. 521/131 RG; 570/123; 570/134
(58) Field of Search .......................... 570/123, 134; 521/131

(56) References Cited

U.S. PATENT DOCUMENTS

| 5,574,192 A | * 11/1996 | VanDerPuy et al. |
| 5,837,743 A | * 11/1998 | Londrigan et al. |
| 5,917,098 A | * 6/1999 | Bertocchio et al. |
| 6,080,799 A | 6/2000 | Kruecke et al. ............. 521/131 |

* cited by examiner

Primary Examiner—Johann Richter
Assistant Examiner—Sikarl A. Witherspoon
(74) Attorney, Agent, or Firm—Colleen Szuch

(57) ABSTRACT

The invention relates to mixtures of 1,1,1,3,3-pentafluoropropane and 1,1,1,3,3-pentafluorobutane. The blends are useful as blowing agents for polymer foam, solvents, aerosol propellants and heat transfer media.

2 Claims, 1 Drawing Sheet

MIXTURES CONTAINING 1,1,1,3,3-PENTAFLUOROPROPANE AND 1,1,1,3,3-PENTAFLUOROBUTANE

FIELD OF THE INVENTION

Figure 1:
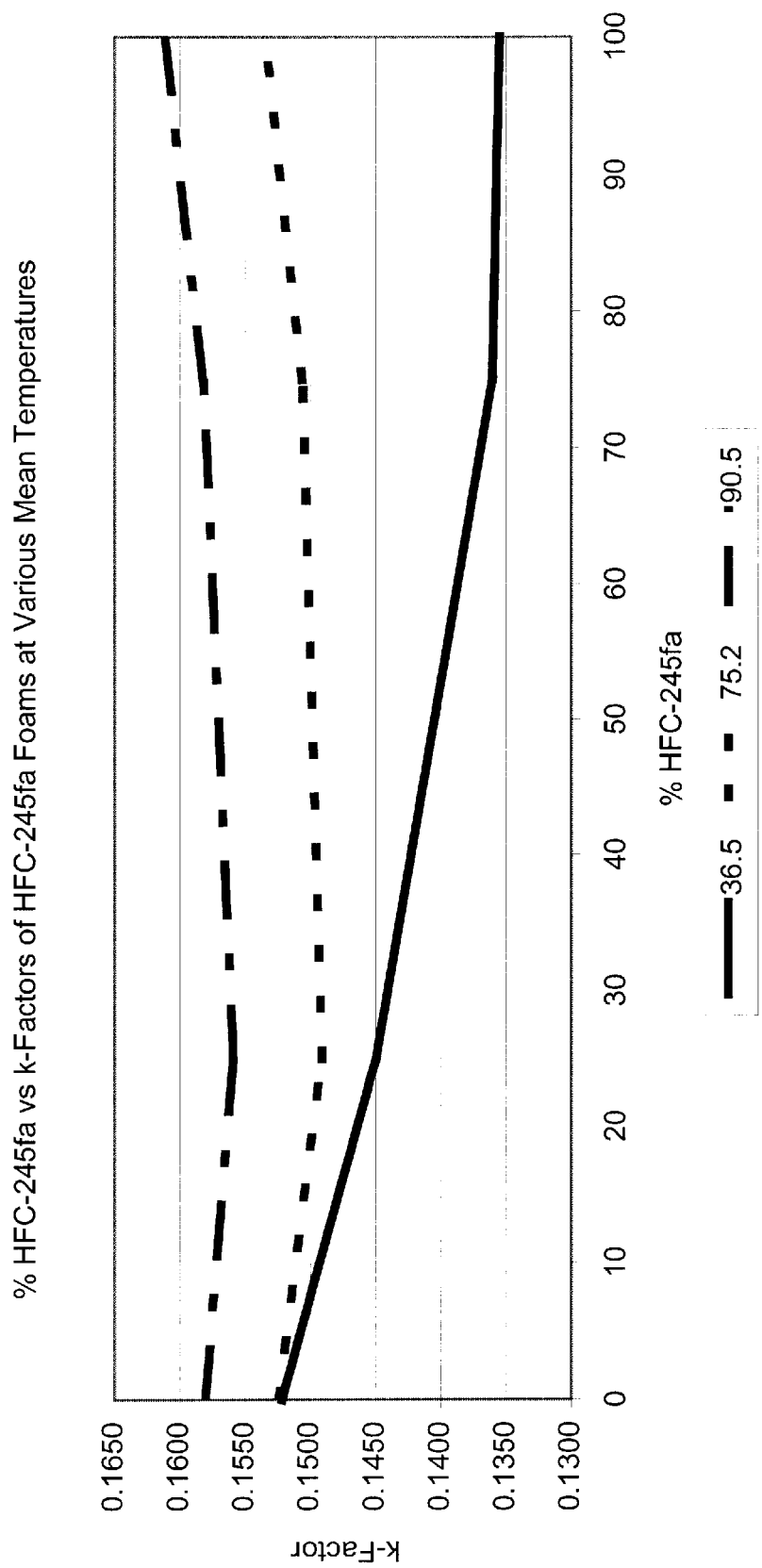

The invention relates to mixtures of 1,1,1,3,3-pentafluoropropane and 1,1,1,3,3-pentafluorobutane. More particularly the invention relates to blowing agent compositions containing 1,1,1,3,3-pentafluoropropane and 1,1,1,3,3-pentafluorobutane.

BACKGROUND

The class of foams known as low density rigid polyurethane or polyisocyanurate foam has utility in a wide variety of insulation applications including roofing systems, building panels, refrigerators and freezers. A critical factor in the large-scale commercial acceptance of rigid polyurethane foams in the building insulation industry has been their ability to provide a good balance of properties. Rigid polyurethane and polyisocyanurate foams are known to provide outstanding thermal insulation, excellent fire properties and superior structural properties at reasonably low densities.

The methods of producing polyurethane and polyisocyanurate foams are generally known and consist in general of the reaction of an organic polyisocyanurate (including diisocyanate) and a polyol or mixture of polyols in the presence of a volatile blowing agent, which is caused to vaporize by the heat liberated during the reaction of isocyanate and polyol. This reaction can be enhanced through the use of amine and/or other catalysts as well as surfactants. The catalysts ensure adequate curing of the foam, while the surfactants regulate and control cell size. Flame-retardants are traditionally added to rigid polyurethane or polyisocyanurate foam to reduce its flammability.

The foam industry has historically used liquid fluorocarbon blowing agents such as trichlorofluoromethane (CFC-11) and 1,1-dichloro-1-fluoroethane (HCFC-141b) because of their ease of use in processing conditions. Fluorocarbons act not only as blowing agents by virtue of their volatility, but also are encapsulated or entrained in the closed cell structure of the rigid foam and are the major contributor to the low thermal conductivity properties of rigid urethane foams.

The use of a fluorocarbon as the preferred commercial expansion or blowing agent in insulating foam applications is based in part on the resulting k-factor associated with the foam produced. K-factor is defined as the rate of transfer of heat energy by conduction through one square foot of one inch thick homogenous material in one hour where there is a difference of one degree Fahrenheit perpendicularly across the two surfaces of the material. Since the utility of closed-cell polyurethane-type foams is based, in part, upon their thermal insulation properties, it would be advantageous to identify materials that produce lower k-factor foams.

1,1,1,3,3-pentafluoropropane (HFC-245fa) and 1,1,1,3,3-pentafluorobutane (HFC-365mfc) are known blowing agents. See U.S. Pat. Nos. 5,496,866; 5,574,192; 5,917,098; and 6,080,799, herein incorporated by reference in their entirety.

It has now been discovered that foams prepared with a blowing agent comprising a blend of HFC-245fa and HFC-365mfc, wherein HFC-245 is present in a major amount, exhibit improved k-factor over both HFC-365mfc and HFC-245fa alone. The improvement is non-linear, which is unexpected since the mixture is non-azeotropic.

SUMMARY

The invention provides mixtures comprising, consisting essentially of or consisting of 1,1,1,3,3-pentafluoropropane (HFC-245fa) and 1,1,1,3,3-pentafluorobutane (HFC-365mfc). Preferably, the compositions comprise from about 51 to about 99 weight percent 1,1,1,3,3-pentafluoropropane and from about 1 to about 49 weight percent 1,1,1,3,3-pentafluorobutane. More preferably, the compositions comprise from about 75 to about 99 weight percent 1,1,1,3,3-pentafluoropropane and from about 1 to about 25 weight percent 1,1,1,3,3-pentafluorobutane.

In one embodiment, the invention provides a blowing agent comprising the composition of the invention.

In another embodiment, the invention provides a method of preparing foam compositions based on isocyanate which comprises reacting and foaming a mixture of ingredients which will react to form polyurethane or polyisocyanurate foams in the presence of the blowing agent composition of the invention.

In yet another embodiment, the invention provides a closed cell foam prepared from a polymer foam formulation containing the blowing agent composition of the invention.

In yet another embodiment, the invention provides a polyol premix composition comprising a polyol and the blowing agent composition of the invention.

FIGURES

FIG. 1 is a plot of k-factor as a function of weight percent HFC-245fa in the blowing agent composition of the invention at various temperatures.

DESCRIPTION

With respect to the preparation of rigid or flexible polyurethane or polyisocyanurate foams using hydrofluorocarbons as the blowing agent, any of the methods well known in the art can be employed. See Saunders and Frisch, Volumes I and II Polyurethanes Chemistry and Technology (1962). In general, polyurethane or polyisocyanurate foams are prepared by combining an isocyanate, a polyol or mixture of polyols, a blowing agent or mixture of blowing agents, and other materials such as catalysts, surfactants, and optionally, flame retardants, colorants, or other additives.

It is convenient in many applications to provide the components for polyurethane or polyisocyanurate foams in pre-blended foam formulations. Most typically, the foam formulation is pre-blended into two components. The isocyanate or polyisocyanate composition comprises the first component, commonly referred to as the "A" component. The polyol or polyol mixture, surfactant, catalysts, blowing agents, flame retardant, and other isocyanate reactive components comprise the second component, commonly referred to as the "B" component. While the surfactant, catalyst(s) and blowing agent are usually placed on the polyol side, they may be placed on either side, or partly on one side and partly on the other side. Accordingly, polyurethane or polyisocyanurate foams are readily prepared by bringing together the A and B side components either by hand mix, for small preparations, or preferably machine mix techniques to form blocks, slabs, laminates, pour-in-place panels and other items, spray applied foams, froths, and the like. Optionally, other ingredients such as fire retardant, colorants, auxiliary blowing agents, water, and even other polyols can be added as a third stream to the mix head or reaction site. Most conveniently, however, they are all incorporated into one B component.

Any organic polyisocyanate can be employed in polyurethane or polyisocyanurate foam synthesis inclusive of aliphatic and aromatic polyisocyanates. Preferred, as a class is the aromatic polyisocyanates. Preferred polyisocyanates for rigid polyurethane or polyisocyanurate foam synthesis are the polymethylene polyphenyl isocyanates, particularly the mixtures containing from about 30 to about 85 percent by weight of methylenebis(phenyl isocyanate) with the remainder of the mixture comprising the polymethylene polyphenyl polyisocyanates of functionality higher than 2. Preferred polyisocyanates for flexible polyurethane foam synthesis are toluene diisocyanates including, without limitation, 2,4-toluene diisocyanate, 2,6-toluene diisocyanate, and mixtures thereof.

Typical polyols used in the manufacture of rigid polyurethane foams include, but are not limited to, aromatic amino-based polyether polyols such as those based on mixtures of 2,4- and 2,6-toluenediamine condensed with ethylene oxide and/or propylene oxide. These polyols find utility in pour-in-place molded foams. Another example is aromatic alkylamino-based polyether polyols such as those based on ethoxylated and/or propoxylated aminoethylated nonylphenol derivatives. These polyols generally find utility in spray applied polyurethane foams. Another example is sucrose-based polyols such as those based on sucrose derivatives and/or mixtures of sucrose and glycerine derivatives condensed with ethylene oxide and/or propylene oxide. These polyols generally find utility in pour-in-place molded foams.

Typical polyols used in the manufacture of flexible polyurethane foams include, but are not limited to, those based on glycerol, ethylene glycol, trimethylolpropane, ethylene diamine, pentaerythritol, and the like condensed with ethylene oxide, propylene oxide, butylene oxide, and the like. These are generally referred to as "polyether polyols". Another example is the graft copolymer polyols, which include, but are not limited to, conventional polyether polyols with vinyl polymer grafted to the polyether polyol chain. Yet another example is polyurea modified polyols which consist of conventional polyether polyols with polyurea particles dispersed in the polyol.

Examples of polyols used in polyurethane modified polyisocyanurate foams include, but are not limited to, aromatic polyester polyols such as those based on complex mixtures of phthalate-type or terephthalate-type esters formed from polyols such as ethylene glycol, diethylene glycol, or propylene glycol. These polyols are used in rigid laminated boardstock, and may be blended with other types of polyols such as sucrose-based polyols, and used in polyurethane foam applications.

Catalysts used in the manufacture of polyurethane foams are typically tertiary amines including, but not limited to, N-alkylmorpholines, N-alkylalkanolamines, N,N-dialkylcyclohexylamines, and alkylamines where the alkyl groups are methyl, ethyl, propyl, butyl and the like and isomeric forms thereof, as well as heterocyclic amines. Typical, but not limiting, examples are triethylenediamine, tetramnethylethylenediamine, bis(2-dimethylaminoethyl) ether, triethylamine, tripropylamine, tributylamine, triamylamine, pyridine, quinoline, dimethylpiperazine, piperazine, N,N-dimethylcyclohexylamine, N-ethylmorpholine, 2-methylpiperazine, N,N-dimethylethanolamine, tetramethylpropanediamine, methyltriethylenediamine, and mixtures thereof.

Optionally, non-amine polyurethane catalysts are used. Typical of such catalysts are organometallic compounds of lead, tin, titanium, antimony, cobalt, aluminum, mercury, zinc, nickel, copper, manganese, zirconium, and mixtures thereof. Exemplary catalysts include, without limitation, lead 2-ethylhexoate, lead benzoate, ferric chloride, antimony trichloride, and antimony glycolate. A preferred organo-tin class includes the stannous salts of carboxylic acids such as stannous octoate, stannous 2-ethylhexoate, stannous laurate, and the like, as well as dialkyl tin salts of carboxylic acids such as dibutyl tin diacetate, dibutyl tin dilaurate, dioctyl tin diacetate, and the like.

In the preparation of polyisocyanurate foams, trimerization catalysts are used for the purpose of converting the blends in conjunction with excess A component to polyisocyanurate-polyurethane foams. The trimerization catalysts employed can be any catalyst known to one skilled in the art including, but not limited to, glycine salts and tertiary amine trimerization catalysts, alkali metal carboxylic acid salts, and mixtures thereof. Preferred species within the classes are potassium acetate, potassium octoate, and N-(2-hydroxy-5-nonylphenol)methyl-N-methylglycinate.

Dispersing agents, cell stabilizers, and surfactants may be incorporated into the blowing agent mixture. Surfactants, better known as silicone oils, are added to serve as cell stabilizers. Some representative materials are sold under the names of DC- 193, B-8404, and L-5340 which are, generally, polysiloxane polyoxyalkylene block co-polymers such as those disclosed in U.S. Pat. Nos. 2,834,748, 2,917,480, and 2,846,458.

Other optional additives for the blowing agent mixture may include flame retardants such as tris(2-chloroethyl) phosphate, tris (2-chloropropyl) phosphate, tris (2,3-dibromopropyl) phosphate, tris (1,3-dichloropropyl) phosphate, diammonium phosphate, various halogenated aromatic compounds, antimony oxide, aluminum trihydrate, polyvinyl chloride, and the like. Other optional ingredients may include from 0 to about 3 percent water, which chemically reacts with the isocyanate to produce carbon dioxide. The carbon dioxide acts as an auxiliary-blowing agent.

Also included in the mixture are blowing agents. Generally speaking, the amount of blowing agent present in the blended mixture is dictated by the desired foam densities of the final polyurethane or polyisocyanurate foams products. The polyurethane foams produced can vary in density from about 0.5 pound per cubic foot to about 40 pounds per cubic foot, preferably from about 1.0 to about 20.0 pounds per cubic foot, and most preferably from about 1.5 to about 6.0 pounds per cubic foot for rigid polyurethane foams and from about 1.0 to about 4.0 pounds per cubic foot for flexible foams. The density obtained is a function of how much of the blowing agent, or blowing agent mixture, is present in the A and/or B components, or that is added at the time the foam is prepared.

In another embodiment, the mixtures and compositions of this invention may be used as propellants in sprayable compositions, either alone or in combination with known propellants. The sprayable composition comprises, consists essentially of, and consists of a material to be sprayed and a propellant comprising, consisting essentially of, and consisting of a mixture or composition of the invention. Inert ingredients, solvents, and other materials may also be present in the sprayable mixture. Preferably, the sprayable composition is an aerosol. Suitable materials to be sprayed include, without limitation, cosmetic materials such as deodorants, perfumes, hair sprays, cleansers, and polishing agents as well as medicinal materials such as anti-asthma and anti-halitosis medications.

The compositions of the invention may also be used in a method of dissolving a contaminant or removing a contaminant from the surface of a substrate that comprises, consists essentially of, and consists of the step of contacting the substrate with the compositions of the present invention.

EXAMPLE

The invention is further illustrated by the following examples, in which parts or percentages are by weight unless otherwise specified. The following materials were used in the examples.

Polyol: A polyester polyol with an OH number of 240 containing a compatibilizer to aid miscibility, commercially available from Stepan.

Fire Retardant: A chloropropyl phosphate available from Akzo Nobel.

HFC-245fa: 1,1,1,3,3-pentafluoropropane available from Honeywell International Inc.

HFC-365: 1,1,1,3,3-pentafluorobutane available from Solvay.

Surfactant A: A polysiloxane polyether copolymer commercially available from Goldschmidt.

Catalyst A: An inorganic potassium based amine commercially available from Air Products.

Catalyst B: A trimerization catalyst commercially available from Air Products.

Example 1

In this example, rigid polyisocyanurate foams were prepared using the formulation shown in Table 1.

The foams were prepared by a general procedure commonly referred to as "handmixing". For each blowing agent or blowing agent pair, a premix of polyol, surfactant, and catalysts was prepared in the same proportions displayed in Table 1. About 100 grams of each formulation was blended. The premix was blended in a 32oz paint can, and stirred at about 1500 rpm with a Conn 2" diameter ITC mixer until a homogeneous blend was achieved. When mixing was complete, the can was covered and placed in a refrigerator controlled at 32° F. The foam blowing agent or pre-blended pair of blowing agents was also stored in pressure bottles at 32° F. The A-component was kept in sealed containers at 70° F.

The pre-cooled blowing agent was added in the required amount to the premix. The contents were stirred for two minutes with a Conn 2" ITC mixing blade turning at 1000 rpm. Following this, the mixing vessel and contents were re-weighed. If there was a weight loss, the blowing agent or the blend was added to the solution to make up any weight loss. The can is than covered and replaced in the refrigerator.

After the contents have cooled again to 50° F., approximately 10 minutes, the mixing vessel was removed from refrigerator and taken to the mixing station. A pre-weighted portion of A-component, isocyanurate, was added quickly to the B-component, the ingredients mixed for 10 seconds using a Conn 2" diameter ITC mixing blade at 3000 rpm and poured into a 8"×8"×4" cardboard cake box and allowed to rise. Cream, initiation, gel and tack free times were recorded for the individual polyurethane foam samples.

The foams were allowed to cure in the boxes at room temperature for at least 24 hours. After curing, the blocks were trimmed to a uniform size and densities measured. Any foams that did not meet the density specification 1.7±0.1 lb/ft$^3$ were discarded and new foams were prepared.

After ensuring that all the foams meet the density specifications, the foams were tested for k-factor according to ASTM C518. The k-factor results are listed in Table 1.

TABLE 1

| B-side (wt. %) | Experiment 1 | Experiment 2 | Experiment 3 | Experiment 4 |
| --- | --- | --- | --- | --- |
| Polyol | 66.05 | 66.36 | 67.02 | 69.39 |
| Catalyst A | 0.2 | 0.2 | 0.2 | 0.20 |
| Catalyst B | 2.38 | 2.39 | 2.41 | 2.43 |
| Water | 0.33 | 0.33 | 0.34 | 0.34 |
| Surfactant A | 1.32 | 1.33 | 1.34 | 1.35 |
| Fire retardant | 3.30 | 3.32 | 3.35 | 3.37 |
| HFC-245fa | 0 | 6.17 | 18.57 | 24.93 |
| HFC-365mfc | 26.42 | 19.91 | 6.77 | 0 |
| Index | 250 | 250 | 250 | 250 |
| Density | 1.7 | 1.7 | 1.7 | 1.7 |
| k-Factor @ 75.2° F. Initial | .1525 | .1491 | .1506 | .1535 |
| k-Factor @ 90.5° F. Initial | .1581 | .1559 | .1582 | .1612 |

FIG. 1 shows that the k-factor of a foam produced with a mixture of HFC-365mfc and HFC-245fa is unexpectedly lower than that achieved with either material neat. Particularly surprising is the advantageously lower k-factor of foams produced with a mixture of HFC-245fa and HFC-365mfc at lower temperatures.

What is claimed is:

1. A composition of matter comprising from about 51 to about 99 weight percent 1,1,1,3,3-pentafluoropropane and from about 1 to about 49 weight percent 1,1,1,3,3-pentafluorobutane.

2. The composition of claim 1 wherein the 1,1,1,3,3-pentafluoropropane is present in an amount of from about 75 to about 99 weight percent and the 1,1,1,3,3-pentafluorobutane is present in an amount of from about 1 to about 25 weight percent.

* * * * *